US010032388B2

(12) United States Patent
Sommers et al.

(10) Patent No.: US 10,032,388 B2
(45) Date of Patent: Jul. 24, 2018

(54) AUGMENTED AND MEDIATED REALITY WELDING HELMET SYSTEMS

(71) Applicant: ILLINOIS TOOL WORKS INC., Glenview, IL (US)

(72) Inventors: Eric Thomas Sommers, Appleton, WI (US); Nishank Rudresh Patel, Appleton, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 355 days.

(21) Appl. No.: 14/561,770

(22) Filed: Dec. 5, 2014

(65) Prior Publication Data
US 2016/0163221 A1    Jun. 9, 2016

(51) Int. Cl.
*G09B 19/24* (2006.01)
*G02B 27/01* (2006.01)
*G09B 19/00* (2006.01)
*A61F 9/06* (2006.01)
*G06F 3/01* (2006.01)
*G09B 5/02* (2006.01)
*B23K 9/32* (2006.01)
*B23K 9/09* (2006.01)
*B23K 9/095* (2006.01)

(52) U.S. Cl.
CPC .............. *G09B 19/00* (2013.01); *A61F 9/06* (2013.01); *B23K 9/0956* (2013.01); *B23K 9/322* (2013.01); *G02B 27/0172* (2013.01); *G02B 27/0176* (2013.01); *G06F 3/011* (2013.01); *G09B 5/02* (2013.01); *B23K 9/09* (2013.01); *B23K 9/0953* (2013.01); *G02B 2027/0138* (2013.01); *G02B 2027/0178* (2013.01); *G09B 19/24* (2013.01)

(58) Field of Classification Search
CPC .. G09B 19/24; G02B 27/017; G02B 27/0176; B23K 9/322
USPC .................................................. 434/234, 219
See application file for complete search history.

(56) References Cited

U.S. PATENT DOCUMENTS

| 2,045,800 A | 6/1936 | Walther |
| 2,045,802 A | 6/1936 | Walther |
| 2,351,910 A | 6/1944 | Blankenbuehler |

(Continued)

FOREIGN PATENT DOCUMENTS

| CA | 2762296 | 6/2013 |
| DE | 2442998 | 3/1976 |

(Continued)

OTHER PUBLICATIONS

Hillers, et al. "TEREBES: Welding helmet with AR capabilities." Proceedings / Virtual and Augmented Reality Status Conference 2004 : [Leipzig, Feb. 19-20, 2004] / Federal Ministry of Education and Research.*

(Continued)

*Primary Examiner* — Robert J Utama
(74) *Attorney, Agent, or Firm* — McAndrews, Held & Malloy, Ltd.

(57) ABSTRACT

A welding helmet system is provided. The welding helmet system includes a protective shell and a welding display system. The welding display system is configured to be removably coupled to the protective shell. The welding display system is configured to receive data from a sensor, and to display a welding metric derived from the sensor via the image generation system.

15 Claims, 6 Drawing Sheets

(56) References Cited

U.S. PATENT DOCUMENTS

| | | | |
|---|---|---|---|
| 3,943,573 A | 3/1976 | Budmiger | |
| 4,039,254 A | 8/1977 | Harsch | |
| 4,101,979 A | 7/1978 | Tarrone | |
| 4,124,944 A | 11/1978 | Blair | |
| 4,153,913 A * | 5/1979 | Swift | A42B 3/042 348/115 |
| 4,237,557 A | 12/1980 | Gordon | |
| 4,293,757 A | 10/1981 | Niemi | |
| 4,555,614 A | 11/1985 | Morris | |
| 4,559,555 A | 12/1985 | Schoolman | |
| 4,620,322 A | 11/1986 | Eggenschwiler | |
| 4,641,292 A | 2/1987 | Tunnell | |
| 4,677,277 A | 6/1987 | Cook | |
| 4,679,255 A | 7/1987 | Kuhlman | |
| 4,716,273 A | 12/1987 | Paton | |
| 4,721,947 A | 1/1988 | Brown | |
| 4,863,244 A | 9/1989 | Fuerthbauer | |
| 5,189,735 A | 3/1993 | Corona | |
| 5,248,880 A | 9/1993 | Fergason | |
| 5,317,643 A | 5/1994 | Patricelli | |
| 5,444,232 A | 8/1995 | Gunz | |
| 5,533,206 A * | 7/1996 | Petrie | A61F 9/064 2/8.5 |
| 5,644,324 A | 7/1997 | Maguire | |
| 5,708,460 A | 1/1998 | Young | |
| 5,734,421 A * | 3/1998 | Maguire, Jr. | G06F 3/011 345/8 |
| 5,825,441 A | 10/1998 | Hornell | |
| 5,845,053 A | 12/1998 | Watanabe | |
| 5,877,825 A | 3/1999 | Kotler | |
| 5,949,388 A * | 9/1999 | Atsumi | G02B 27/0172 345/53 |
| 6,067,129 A | 5/2000 | Fergason | |
| 6,070,264 A | 6/2000 | Hamilton | |
| 6,078,021 A | 6/2000 | Chang | |
| 6,242,711 B1 | 6/2001 | Cooper | |
| 6,456,261 B1 | 9/2002 | Zhang | |
| 6,552,316 B1 | 4/2003 | Bae | |
| 6,614,409 B1 | 9/2003 | Bae | |
| 6,710,298 B2 | 3/2004 | Eriksson | |
| 6,734,393 B1 | 5/2004 | Friedl | |
| 6,881,939 B1 | 4/2005 | Hamilton | |
| 6,941,577 B2 | 9/2005 | Ackermann | |
| 7,150,047 B2 | 12/2006 | Fergason | |
| 7,161,135 B2 | 1/2007 | Fergason | |
| 7,209,039 B2 | 4/2007 | Krebs | |
| 7,212,300 B2 | 5/2007 | Comer | |
| 7,265,746 B2 | 9/2007 | Knowles | |
| 7,271,894 B2 | 9/2007 | Devitt | |
| 7,298,535 B2 | 11/2007 | Kuutti | |
| 7,342,210 B2 | 3/2008 | Fergason | |
| 7,383,654 B2 | 6/2008 | Olivier | |
| 7,402,786 B2 | 7/2008 | Schofield | |
| 7,411,154 B2 | 8/2008 | Fosbinder | |
| 7,501,613 B2 | 3/2009 | Fergason | |
| 7,534,005 B1 * | 5/2009 | Buckman | A61F 9/068 2/8.2 |
| 7,550,698 B2 | 6/2009 | Fergason | |
| 7,683,290 B2 | 3/2010 | Daniel | |
| 7,926,118 B2 | 4/2011 | Becker | |
| 8,009,229 B1 | 8/2011 | Peterson | |
| 8,569,655 B2 | 10/2013 | Cole | |
| 8,747,116 B2 | 6/2014 | Zboray | |
| RE45,062 E * | 8/2014 | Maguire, Jr. | G06F 3/011 345/8 |
| 8,834,168 B2 | 9/2014 | Peters | |
| 8,851,896 B2 | 10/2014 | Wallace | |
| 8,911,237 B2 | 12/2014 | Postlethwaite | |
| 8,915,740 B2 | 12/2014 | Zboray | |
| 9,323,056 B2 * | 4/2016 | Williams | G02B 27/017 |
| 2002/0124271 A1 | 9/2002 | Herrmann | |
| 2003/0001950 A1 | 1/2003 | Eriksson | |
| 2003/0011673 A1 | 1/2003 | Eriksson | |
| 2003/0083112 A1 | 5/2003 | Fukuda | |
| 2003/0206491 A1 | 11/2003 | Pacheco | |
| 2004/0008157 A1 * | 1/2004 | Brubaker | G02B 27/0176 345/8 |
| 2005/0001155 A1 | 1/2005 | Fergason | |
| 2005/0005308 A1 | 1/2005 | Logan | |
| 2005/0007504 A1 | 1/2005 | Fergason | |
| 2006/0203148 A1 | 9/2006 | Magnusson | |
| 2007/0056072 A1 | 3/2007 | Steinemann | |
| 2007/0056073 A1 | 3/2007 | Martin | |
| 2007/0080621 A1 | 4/2007 | Huh | |
| 2007/0086508 A1 | 4/2007 | Reading | |
| 2008/0120752 A1 | 5/2008 | Huh | |
| 2008/0158502 A1 | 7/2008 | Becker | |
| 2008/0169277 A1 | 7/2008 | Achtner | |
| 2009/0094721 A1 | 4/2009 | Becker | |
| 2009/0231423 A1 | 9/2009 | Becker | |
| 2009/0276930 A1 | 11/2009 | Becker | |
| 2009/0298024 A1 * | 12/2009 | Batzler | B23K 9/32 434/234 |
| 2010/0062406 A1 * | 3/2010 | Zboray | G09B 19/24 434/234 |
| 2011/0083241 A1 | 4/2011 | Cole | |
| 2011/0183304 A1 | 7/2011 | Wallace | |
| 2011/0186615 A1 | 8/2011 | Gatlin | |
| 2012/0081564 A1 * | 4/2012 | Kamiya | G02B 27/017 348/216.1 |
| 2012/0291172 A1 * | 11/2012 | Wills | B23K 9/0956 2/8.2 |
| 2013/0009993 A1 | 1/2013 | Horseman | |
| 2013/0291271 A1 | 11/2013 | Becker | |
| 2014/0007312 A1 | 1/2014 | Wright | |
| 2014/0346158 A1 | 11/2014 | Matthews | |
| 2015/0056584 A1 | 2/2015 | Boulware | |
| 2015/0234189 A1 * | 8/2015 | Lyons | G02B 27/0172 345/174 |
| 2015/0268473 A1 * | 9/2015 | Yajima | G02B 27/0172 345/633 |
| 2016/0081856 A1 | 3/2016 | Hofer-Kraner | |
| 2016/0165220 A1 * | 6/2016 | Fujimaki | G09G 3/36 348/49 |
| 2016/0188277 A1 * | 6/2016 | Miyasaka | G06F 3/1438 345/2.2 |
| 2016/0260261 A1 * | 9/2016 | Hsu | G06T 19/006 |
| 2017/0045337 A1 * | 2/2017 | Kim | F41H 11/12 |

FOREIGN PATENT DOCUMENTS

| | | |
|---|---|---|
| EP | 0335056 | 10/1989 |
| EP | 0963744 | 12/1999 |
| EP | 1025946 | 8/2000 |
| WO | 0061044 | 10/2000 |
| WO | 0158399 A1 | 8/2001 |
| WO | 2005102230 A1 | 11/2005 |
| WO | 2014188244 | 11/2014 |

OTHER PUBLICATIONS

Fast et al., Virtual Training for Welding, Proceedings of the Third IEEE and ACM International Symposium on Mixed and Augmented Reality (ISMAR 2004); 0-7695-2191-6/04; 2004.

International Search Report from PCT application No. PCT/US2015/059446, dated Jan. 22, 2016, 13 pgs.

* cited by examiner

AUGMENTED AND MEDIATED REALITY WELDING HELMET SYSTEMS

BACKGROUND

The present disclosure relates generally to welding helmet systems and, more particularly, to augmented and mediated reality welding helmet systems.

Welding is a process that has increasingly become utilized in various industries and applications. Such processes may be automated in certain contexts, although a large number of applications continue to exist for manual welding operations. In both cases, such welding operations rely on a variety of types of equipment to ensure the supply of welding consumables (e.g., wire feed, shielding gas, etc.) is provided to the weld in appropriate amounts at the desired time.

Welding operations are performed on a variety of different materials using various techniques. For example, a workpiece may be formed from a carbon steel, a corrosion resistant alloy, such as stainless steel, an aluminum, and so on. Certain workpieces may thus benefit from different welding techniques and monitoring. Accordingly, a quality of a weld on a workpiece may depend on more closely monitoring the welding operation. It would be beneficial to improve monitoring capabilities via welding helmet systems.

BRIEF DESCRIPTION

In one embodiment, a welding helmet system is provided. The welding helmet system includes a protective shell and a welding display system. The welding helmet system includes a protective shell and a welding display system. The welding display system is configured to be removably coupled to the protective shell. The welding display system is configured to receive data from a sensor, and to display a welding metric derived from the sensor via the image generation system.

In another embodiment, a welding helmet system includes a protective shell, and a first welding display system configured to be removably coupled to the protective shell. The first welding system is configured to receive data from a sensor. The first welding system is additionally configured to display a welding metric, wherein the welding metric is derived from the data, and to communicate with a second welding display system, with an external system, or a combination thereof.

In a further embodiment, a welding display system is provided. The welding display system includes an image generation system and an attachment system configured to attach and to detach the welding display system to a welding helmet, to a protective face shield, or a combination thereof. The welding display system includes a processor configured to receive data from a sensor, and to display the welding metric via the image generation system, wherein the welding metric is derived from the data.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Embodiments of the present disclosure may be used in any application where it may be desired to more closely monitor welding operations, for example, via enhancements throughout a reality-virtuality continuum of welding and/or training operations. That is, the techniques described herein may be applicable at a reality-only first end of the continuum, where the real environment is presented to a welding operator and/or trainer unmodified, such as through a transparent or semi-transparent screen. The techniques described herein may be further applicable to improve welding operations and/or training by augmenting reality via additional features (e.g., augmented reality features) such as text, graphics, and/or audio superimposed onto the real environment. The techniques described herein may additionally improve welding operations and/or training via a mediated reality, further along the reality-virtuality continuum, where reality may be mediated, for example, by viewing the real world via one or more cameras. Further, the techniques described herein may improve welding operations and/or training via presentation of a full virtual welding environment at an opposite end of the reality-virtuality continuum, where viewable and audio constructs may all be computer generated. By operating throughout the entirety of the reality-virtuality continuum, the improvements disclosed herein may enhance and improve welding operations and welding training.

Advantageously, the techniques described herein include removable, replaceable, and upgradeable inserts and eyeglasses that may be used in conjunction with welding helmets to provide for enhanced visualizations and audible features. The inserts and eyeglasses described herein may be communicatively coupled to a variety of sensors, welding power supplies, and external systems (e.g., cloud-based systems) to provide for visualizations and audio useful in monitoring, for example, a quality of welding operations and/or training. The inserts and eyeglasses may be communicatively coupled to each other to deliver, for example, visual and audio data to other interested parties, such as a supervisor or trainer. Indeed, a variety of welding metrics, user biometrics, and/or environmental metrics may be derived and delivered via the inserts and eyeglasses described herein. It is to be understood that the term welding metric, as described herein, includes images and videos taken by a camera sensor. By providing for a variety of reality-virtuality continuum inserts and eyeglasses, the techniques described herein provide for enhanced welding helmets suitable for more efficiently monitoring welding operations.

Figure 1:
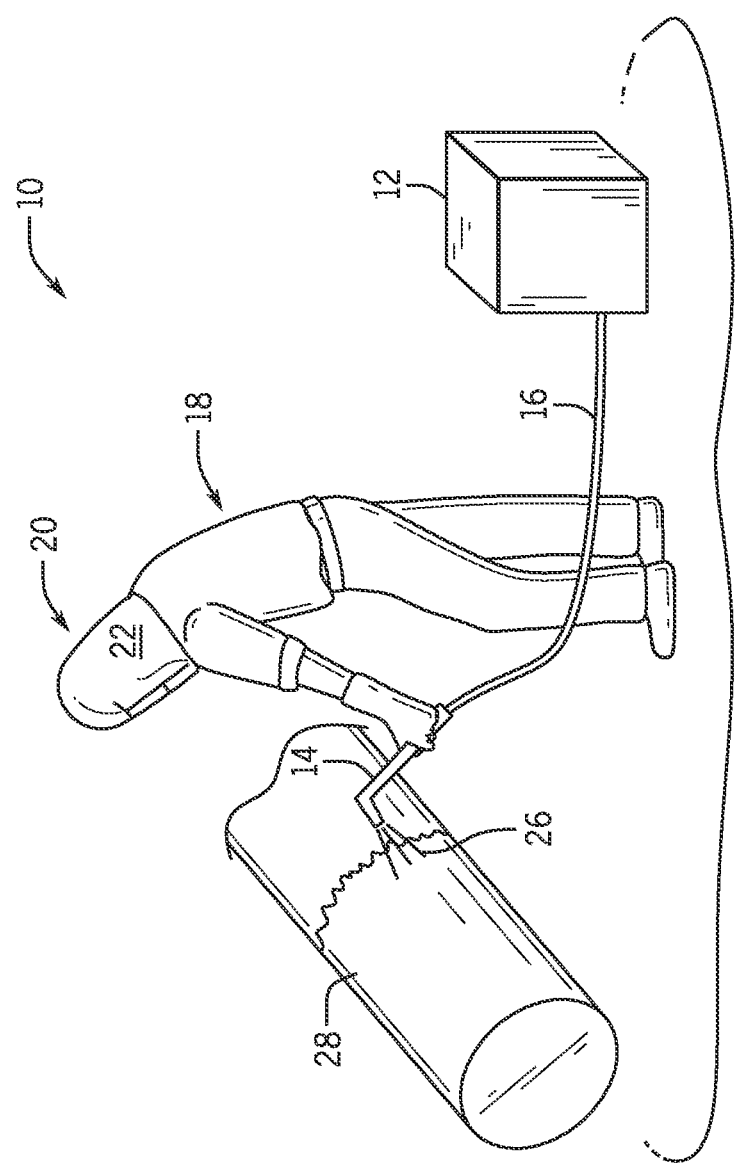
FIG. 1 is an illustration of an embodiment of a welding system including a mediated reality welding helmet, in accordance with aspects of the present disclosure.

Turning now to the figures, FIG. 1 illustrates an embodiment of an arc welding system 10. As depicted, the arc welding system 10 may include a power supply 12 that generates and supplies welding power to an electrode 14 via a conduit 16. In the arc welding system 10, a direct current (DC) or alternating current (AC) may be used along with a consumable or non-consumable electrode 14 to deliver current to the point of welding. In such a welding system 10, an operator 18 may control the location and operation of the electrode 14 by positioning the electrode 14 and triggering the starting and stopping of the current flow. As illustrated, a helmet system 20 is worn by the welding operator 18. The helmet system 20 includes a helmet shell 22 and, in certain embodiments, a lens assembly that may be darkened to prevent or limit exposure to the light generated by a welding arc 26. The helmet system 20 may be coupled to a variety of eyeglasses and inserts, as described in more detail below, to provide for enhanced visuals and audio that work throughout the reality-virtuality continuum. The helmet shell 22 and other protective shells described herein may be made of a variety of materials, including carbon fiber, plastics, leather, fabric materials, or a combination thereof. The protective shells may protect against heat, sparks, light, or a combination thereof.

When the operator 18 begins the welding operation (or other operation such as plasma cutting) by applying power from the power supply 12 to the electrode 14, the welding arc 26 is developed between the electrode 14 and a workpiece 28, such as the illustrated pipe. The workpiece 28 may be formed from a carbon steel or a corrosion resistant alloy, such as stainless steel, or other metals and alloys (e.g., aluminum, titanium, zirconium, niobium, tantalum, nickel alloys). Non-metal (e.g., plastic, polymeric, rubber) workpieces 28 may also be welded or otherwise joined, for example, by stir welding.

Generally, the techniques described herein enable certain operations (e.g., welding, cutting, grinding, induction heating, testing) to be performed on the workpiece 28 by applying power supplied by the power supply 12. The workpiece 28 may be disposed in an industrial facility (e.g., industrial plant, shipyard) but may also be disposed in a residential facility, such as a garage or a home. The workpiece 28 may include tubular pieces (e.g., pipe), flat sheeting (e.g., metal or plastic sheets and plates), angled workpieces 28 (e.g., angle iron) or any other piece that may be welded, cut, ground, induction heated, or tested, for example, by using power delivered via the power supply 12.

The electrode 14 and the conduit 16 thus deliver current and voltage sufficient to create the welding arc 26 between the electrode 14 and the workpiece 28. The welding arc 26 melts the metal (the base material and any filler material added) at the point of welding between the electrode 14 and the workpiece 28, thereby providing a joint when the metal cools. The welding system 10 may be configured to form a weld joint by any suitable technique, including shielded metal arc welding (SMAW) (i.e., stick welding), gas tungsten arc welding (GTAW), gas metal arc welding (GMAW), flux-cored arc welding (FCAW), metal inert gas welding (MIG), tungsten inert gas welding (TIG), gas welding (e.g., oxyacetylene welding), sub-arc welding (SAW), and/or resistance welding. As may be appreciated, shielding gas may be used in certain applications, such as GTAW, GMAW, and FCAW, for example. Waveforms used during welding may include regulated metal deposition (RMD) type waveforms, among others, surface tension transfer (STT), cold metal transfer (CMT).

Figure 2:
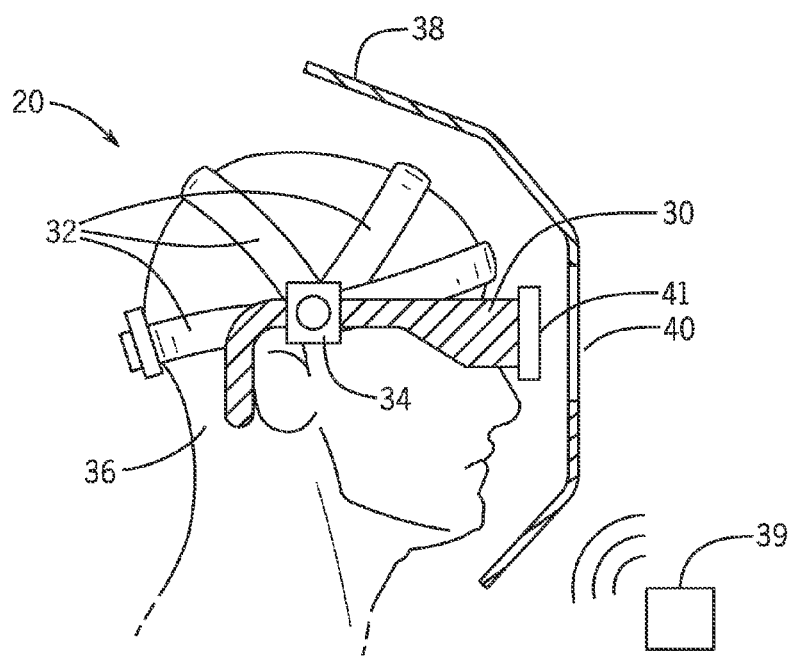
FIG. 2 is a cross-sectional side view of an embodiment of a welding helmet system having detachable augmented reality eyeglasses, in accordance with aspects of the present disclosure.

As mentioned above, the helmet system 20 may include a variety of inserts and eyeglasses that provide for enhanced visualizations and audio during welding operations and welding training. For example, FIG. 2 illustrates an embodiment of the helmet system 20 including detachable augmented reality (AR) safety eyeglasses 30 (e.g., welding display system). The AR eyeglasses 30 may be securely coupled to a headgear assembly 32 via an eyeglass fastener 34 of the headgear assembly 32. The headgear assembly 32 may be adjustable to fit a variety of head 36 sizes and may be coupled to a protective welding helmet shell 38. For example, the headgear assembly 32 (e.g., helmet shell suspension system) may attach to the helmet shell 38 via one or more attachment techniques (e.g., snap fasteners, rotating fasteners, screws, and the like).

In use, the welding operator 18 may attach the AR eyeglasses 30 to the headgear assembly 32 via the eyeglass fastener 34, and then "flip down" the welding helmet shell 38 during welding (or training) activities. A filter screen 40 on the welding helmet shell 38 may attenuate or otherwise filter light from, for example, the welding arc 26, to enable a more suitable view during the welding activities. The AR eyeglasses 30 may include an image generation system 41 suitable for displaying images viewable by the operator 18, and/or a trainer, for example, as an overlay over real world images viewable through the filter screen 40. More specifically, the image generation system 41 may include processors, light projector systems, prisms, and so on, useful in delivering images viewable by the human eye. Accordingly, the real environment (e.g., viewable through the filter screen 40) may be augmented via a variety of useful displays. For example, welding metrics, user biometrics, and/or environmental metrics may be provided as described in more detail below. By deriving and displaying a variety of welding metrics, user biometrics, and/or environmental metrics, welding operations and training may be improved.

Sensors 39 may be communicatively coupled to the AR eyeglasses 30, directly or indirectly via another system (e.g., sensor data transmitted via power supply 12), for example, through wireless protocols (e.g., Bluetooth, IEEE 802.11x [e.g., WiFi], Zigbee, HART, LTE, Z-Wave, WirelessHD, WiGig). The sensors 39 may include sensors 39 disposed on the power supply 12 (e.g., current and voltage sensors), on or about the workpiece 28 (e.g., temperature sensors, optical sensors, x-ray sensors), on the welding helmet shell 38, or on the AR eyeglasses 30 themselves (for example to monitor the operator 18). When disposed on the AR eyeglasses 30 and/or on (e.g., worn by) the operator 18, the sensors 39 may include biometric sensors suitable for deriving user biometrics, for example, heat stress, heart rate (e.g., via pulse oximetry and the like), and other biometric readings of the operator 18. Accordingly, the operator 18 may be monitored, and data relayed to the operator 18 (and third parties) relating to heat stress, heart rate, and the like. Sensors 39 may additionally provide for derivations of environmental metrics, such as surrounding temperature, humidity, ambient pressure, altitude, light levels, gases (e.g., air quality gases), and the like. Indeed, the sensors 39 may include temperature sensors, voltage sensors, current sensors, optical sensors, x-ray sensors, capacitance sensors, inductive sensors, air quality sensors, and the like.

Figure 3:
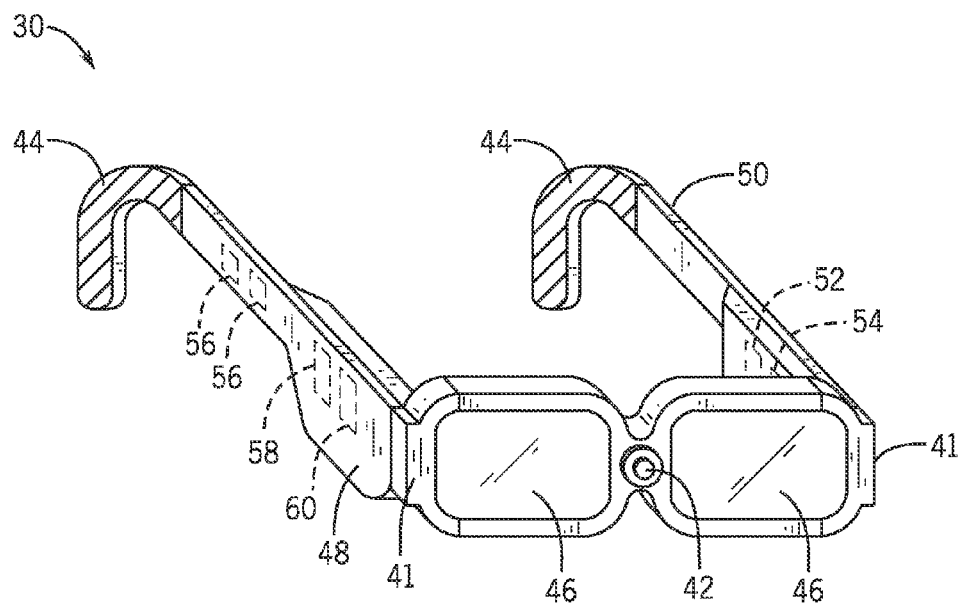
FIG. 3 is a perspective view of an embodiment of the detachable augmented reality eyeglasses of FIG. 2, in accordance with aspects of the present disclosure.

In certain embodiments, the AR eyeglasses 30 may include a camera 42 (e.g., charge coupled device [CCD] sensor) and one or more speakers 44, as shown in FIG. 3. More specifically, FIG. 3 shows a perspective view of the AR eyeglasses 30 having a single camera 42 disposed between lenses 46. It is to be noted that, in other embodiments, one or more cameras 42 may be used, and the cameras 42 may be disposed at various locations, including a right temple 48 and/or a left temple 50 location. It is also to be noted that the lenses 46 may include prescription lenses suitable for adjusting or otherwise correcting vision, and the lenses 46 may be safety lenses suitable for use in industrial environments. Generally, the camera(s) 42 capture the same view as that of the operator 18. The speakers 44 may include bone conduction speakers suitable for conducting sound through bones in the human skull, in-ear speakers disposed inside the ear, over-ear speakers disposed on the ear, or a combination thereof.

In use, the camera(s) 42 may capture images and/or video of welding operations and/or training activities. The captured images and/or video (and all data captured, including sensor 39 data) may then be used, for example, as logging data suitable for certifying a weld quality, and for further analysis. For example, a wired and/or wireless communications system 52 may be used to transmit data to and receive data from external systems (e.g., power supply 12, cloud-based systems, local area network [LAN] workstations/servers, wide area network [WAN] workstation/servers, and so forth). The communications system 52 may include wireless systems such as 802.11x (e.g., WiFi), Zigbee, Z-wave, Bluetooth, cell phone communications systems (e.g., LTE, 4G, CDMA, GSM), and the like. The communications system 52 may also include wired systems such as Ethernet based systems, two-wire systems (e.g., I2C), PCI, 1-wire systems, and the like.

The data transmitted from the AR eyeglasses 30 may include camera 42 data, as well as data from other sensors 39 used to sense welding operations or training. Other sensor data may include temperature data of the workpiece 28, power supply 12 data (e.g., voltage and current used), workorder data (e.g., type of workpiece to be welded, type of weld to be applied, welding supplies to be used), and so on. The data (e.g., camera 42 data and/or sensor 39 data) may be additionally or alternatively processed via processing circuitry 54. Attachment points 56 may be used to attach the AR eyeglasses 30 to the eyeglass fastener 34, and may additionally provide for electrically conductive attachments to provide power to charge batteries 58 that may power the AR eyeglasses 30. For example, power may be provided via an external power supply and/or via other batteries disposed on the welding helmet shell 38, and the attachment points 56 may facilitate power being transferred from such power sources to the AR eyeglasses 30. A user input system 60 may be used by the operator 18 to provide a variety of inputs, such as via head nods, eye winks, touch gestures (e.g., swipes of certain portions the temples 48, 50) and/or voice commands (e.g., via microphone). In one example, voice annotations during welding, as well as voice commands to change voltage and/or current delivered via the power supply 12 may be provided via the input system 60.

Camera 42 data (observing the weld torch 14) and/or sensors 39 may be processed to determine, for example, a welding speed, an angle at which the operator 18 holds the weld torch 14, as well as various weld observations, which, depending on a type of weld (e.g., fillet weld, groove weld, lap weld, plug and slot weld) may include concavity/convexity metrics, cross sectional weld area, leg size, toe angle, undercut metrics, weld face metrics, weld throat metrics, mismatch metrics, bead width metrics, reinforcement height metrics, porosity metrics, and so on, which may be displayed via the image generation system 41 in real-time during welding.

For example, weld speed may be determined by accelerometers on the weld torch 14 and/or via camera 42/sensor 39 observations that identify the weld torch 14 moving with respect to the workpiece 28 or other object. Weld angle may be determined by similar visual observations via camera 42/sensor 39 as well as via one or more gyroscopes disposed in the weld torch 14. Visual observations via camera 42/sensor 39 may also observe if a weld is concave or convex, and measure concavity/convexity thickness, as well as the cross section of a weld area. Likewise, leg size, toe angle, undercut size/shape, weld face metrics, weld throat metrics, mismatch metrics, reinforcement height (e.g., height of bead reinforcement), and/or bead width may be observed and measured, for example, by applying trigonometric calculations. The cameras 42, 74 and/or sensors 39 described herein may include a variety of sensor embodiments, including infrared sensors, x-rays, ultrasound, and the like. Porosity, for example, may be measured via radiology and/or ultrasound.

The camera 42 data processing (e.g., via external systems and/or via the circuitry 54 of the AR eyeglasses 30) may include real-time processing suitable for guiding the operator 18 during welding activities. For example, if the operator 18 is moving the electrode 14 too slowly or too quickly, the AR eyeglasses 30 may then display, via the image generation system 41, certain animations, icons, warnings, text, and so on, notifying the operator 18 of the issue and/or corrective actions to take (e.g., slow down, speed up). The image generation system 41 may additionally display workorder information (e.g., type of workpiece 28, welding supplies to use, and so forth), further instructions, notes, and so on. Likewise, the speakers 44 may be used to provide audio indications, text-to-speech, and other audio suitable for improving welding operations, such as alarms, alerts, voice guidance, and the like.

In one example, the operator 18 may scan a workorder (e.g., workorder barcode) by using the camera(s) 42 and/or by using the input system 60. The AR eyeglasses 30 may then load certain parameters based on the workorder, such as welding supplies to be used, type of weld to be performed, and/or weld parameters (e.g., concavity/convexity metrics, cross sectional weld area, leg size, toe angle, undercut metrics, weld face metrics, weld throat metrics, mismatch metrics, bead width metrics, reinforcement height metrics, porosity metrics, and so forth). The operator 18 may then proceed with the welding operation, with the camera(s) 42 capturing image data. The AR eyeglasses 30 may then use the internal circuitry 54 and/or external systems to derive, via the image data and/or sensor data, a quality of welding. The AR eyeglasses 30 may then inform the operator 18 of the welding operation quality during and/or after the welding operation. Data captured, such as image data, may be stored in a memory medium of the AR eyeglasses 30 and/or external systems (e.g., cloud storage), for example, to certify the weld or for additional data analysis.

The AR eyeglasses 30 may be communicatively coupled to a second pair of AR eyeglasses 30 worn by a supervisor or trainer. Accordingly, the supervisor or trainer may don the second pair of AR eyeglasses 30 and observe the welding or training activities in real-time. Pairing between two or more AR eyeglasses 30 may be initiated by the third-party observer (e.g., supervisor), by the welding operator 18, and/or by the "cloud." For example, the supervisor may don a pair of AR eyeglasses 30 and may then request a list of other AR eyeglasses 30 that are online. In one embodiment, the list is filtered to only include AR eyeglasses 30 located in a given facility or geographic area. The list may additionally be filtered to include only AR eyeglasses 30 that the supervisor (or other entity) has access to. The supervisor may then select a desired pair of AR eyeglass 30 from the list. In one embodiment, the supervisor may then enter additional security information, such as login information, to complete the pairing and to begin viewing data remotely. To unpair AR eyeglasses 30, either one of the supervisor or operator 18 may request to unpair and disconnect via the input system 60, such as through voice command, menus, touches, gestures, and the like.

Voice and/or text feedback may be captured on the supervisor's input system 60 and transmitted to the operator 18 (and vice versa). Likewise, the AR eyeglasses 30 may be communicatively coupled to an external system, such as a cell phone, tablet, computer, notebook, website, cloud-based system, and the like, which may be used by a third party to provide feedback to the operator 18 when wearing the AR eyeglasses 30. Further, the AR eyeglasses 30 may display, via the image generation system 41, welding manuals, training videos, notes, and so on, useful to operate and/or train on the welding system 10. Additionally, the AR eyeglasses 30 may be communicatively coupled to other removable and replaceable AR and/or mediated reality (MR) systems, as described in the more detail below.

Figure 4:
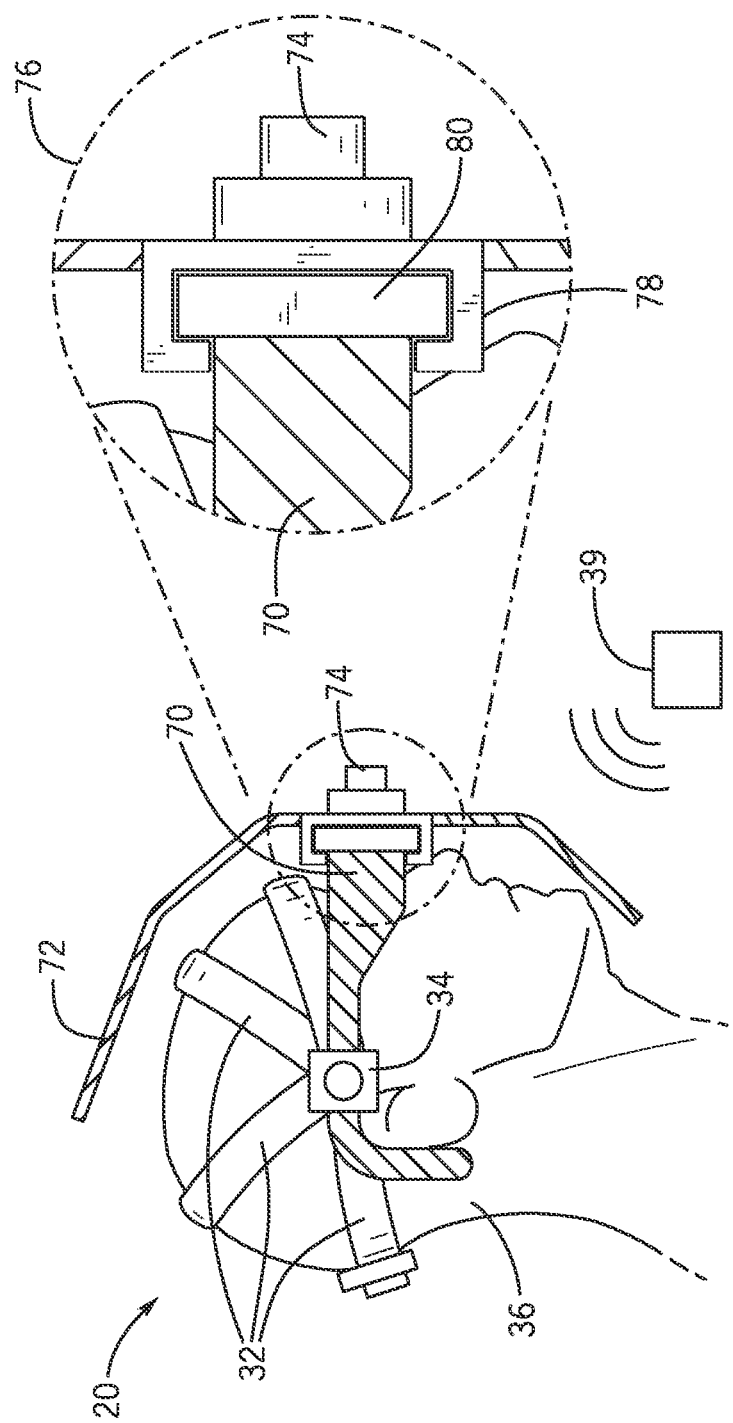
FIG. 4 is a cross-sectional side view of an embodiment of a welding helmet system having detachable augmented reality eyeglasses, in accordance with aspects of the present disclosure.

FIG. 4 depicts an embodiment of the helmet system 20 having MR eyeglasses 70 coupled to a protective welding shell 72. In the depicted embodiment, the MR eyeglasses 70 are coupled to the shell 72 via headgear assembly 32 and eyeglass fastener 34. Unlike the AR eyeglasses 30 that may include transparent or semi-transparent lenses, the MR eyeglasses 70 view data from an external camera(s) 74 mounted on an exterior face of the shell 72, and present the data to the operator 18 and/or other users (e.g., supervisors, trainers). Accordingly, the MR eyeglasses 70 can present data along the mediated portion of the reality-virtuality continuum because the MR eyeglasses 70 may mediate the real environment via the camera(s) 74. For example, when the camera 74 is in use, the MR eyeglasses 70 may display imaging data (e.g., images, video) transmitted from the camera 74 representative of the real world, thus providing for a mediated reality-based imaging. Additionally, the camera 74 data may be further processed, for example, by overlaying data (images, text, icons, and the like) on top of the camera 74 images to further mediate reality, providing for a mediated or mixed reality view.

Further, the MR eyeglasses 70 may provide for an immersive virtual environment, where no camera 74 images are presented and instead, all images are computer-generated in real-time. This virtual reality mode of operations may be particularly useful in training situations. For example, a virtual reality "world" may be presented, including virtual representations of the workpiece 28, the power supply 12, the electrode 14, and other components of the system 10. The operator 18 may then virtually weld the virtual workpiece 28 and receive feedback via the MR eyeglasses 70 representative of weld quality during and/or after the virtual welding operation. For example, the MR eyeglasses 70 may instruct the operator 18 to reposition the electrode 14, to change an angle of the electrode 14, to move the electrode 14 faster or slower, to change power supply parameters (e.g., applying more or less current/voltage, and so on. Likewise, alerts, alarms, and other welding parameters may be displayed. Additionally, third party users may provide feedback (voice, text) while viewing the operator's performance during the virtual welding, for example, through external systems such as cell phones, tablets, computers, notebooks, websites, cloud-based systems, through other AR eyeglasses 30, other MR eyeglasses 70, and the like.

In one embodiment, the virtual world may be created based on a scan of a workorder, or via some other input. The virtual world may include a virtual representation of the type of material to be worked on, the welding supplies to be used, the welding equipment (e.g., system 10) to be used, and/or the work environment (e.g., upside down weld, flat weld, and so on). Accordingly, the operator 18 may train on a virtual world representative of the system 10 and workpiece 28 until a desired weld quality is achieved. The operator 18 may then switch to an augmented-reality mode, a mediated-reality mode and/or a reality-only mode, and proceed with performing the physical weld. In this manner, a more focused and efficient training environment may be provided, better representing the work about to be performed.

FIG. 4 additionally shows further details of a portion 76 of the shell 72 showing an attachment assembly 78 of the shell 72 suitable for attaching the MR eyeglasses 70 when disposed inside of the shell 72. In the depicted embodiment, the MR eyeglasses 70 may include a frame 80 that may be "slid" or otherwise disposed inside of the attachment assembly 78. An interference fit or force, a magnetic force, a spring-bias force, or a combination thereof, may then provide for a secure attachment between the MR eyeglasses 70 and the shell 72 via the attachment assembly 78. Accordingly, movements of the head 36 may then correspondingly move the shell 72, cameras 74, and MR eyeglasses 70 together, thus increasing view fidelity and minimizing view latency. It is to be noted that, in other embodiments, the MR eyeglasses 70 may be used with shells 72 lacking the attachment assembly 78. It is also to be noted that the attachment assembly 78 may be used with the AR eyeglasses 30 above as part of the shell 38, to more securely hold the AR eyeglasses 30 in place when coupled to the shell 38.

Figure 5:
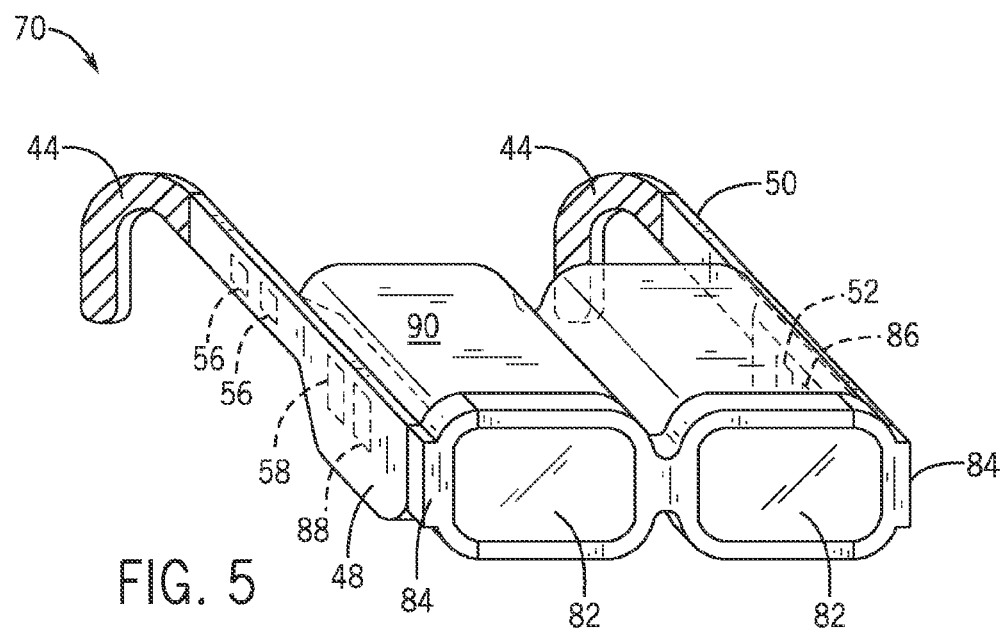
FIG. 5 is a perspective view of an embodiment of the detachable augmented reality eyeglasses of FIG. 4, in accordance with aspects of the present disclosure.

FIG. 5 shows a perspective view of an embodiment of the MR eyeglasses 70, showing certain features in more detail. Because FIG. 5 includes like elements to the figures above, the like elements are shown with like element numbers. It is also to be noted that elements of both the AR eyeglasses 30 and the MR eyeglasses 70 may be used in the other eyeglasses, such as input systems 60, 88, processing systems 54, 86, and the like. In the depicted embodiment, the MR eyeglasses 70 include two displays 82. The displays 82 may include light emitting diode (LED) displays, organic LED (OLED) displays, liquid-crystal display (LCD) displays, or a combination thereof, suitable for displaying images and/or video. For example, the displays 82 may provide for a field of vision (FOV) between 50 and 180 degrees horizontal at resolutions between 800 to 8K horizontal and 800 to 8K vertical at desired aspect ratios (e.g., 1:1, 5:4, 4:3, 3:3, 16:9, 16:10, and so on). Accordingly, an image generation system 84 may include circuitry suitable for driving the displays 82. In one example, a processing circuitry 86, for example, in combination with the image generation system 84, may drive images via the displays 82 to achieve a latency (e.g., time between head movements and corresponding movement of virtual embodiments displayed) of between 125 Hz and 2000 Hz.

Indeed, an input system 88 may track head movement to derive a desired viewing orientation, and thus change the data (e.g., virtual world) on the displays 82 accordingly to match the viewing orientation. In this manner, the operator 18 may more naturally move the head 36 with a correlative change in the view presented by the displays 82. Also shown is a light blockage housing 90 suitable for minimizing or eliminating external light sources impinging upon the displays 82, thus presenting more generated light to the operator 18. It is to be noted that the eyeglasses 30 and 70 may be communicatively coupled to each other. Accordingly, the screens 82 may view imaging data (or other data) captured via the AR eyeglasses 30, and the AR eyeglasses 30 may display imaging data (or other data) captured via the MR eyeglasses 70.

As mentioned earlier, the cameras 74 may capture imaging data for presentation via the displays 82 and/or for transmission (e.g., via communications system 52) to external systems for data capture and further analysis, similar to the data capture and analysis described above with respect to the AR eyeglasses 30. Indeed, similar to the AR eyeglasses 30, the camera 74 data may be processed to determine, for example, a weld speed, an angle at which the operator 18 holds the electrode 14, as well as various weld observations, which, depending on a type of weld (e.g., fillet weld, groove weld, lap weld, plug and slot weld) may include concavity/convexity metrics, cross sectional weld area, leg size, toe angle, undercut metrics, weld face metrics, weld throat metrics, mismatch metrics, bead width metrics, reinforcement height metrics, porosity metrics, and so on, which may be displayed via the image generation system 84 in real-time (and transmitted to external systems via system 52). The camera data processing (e.g., via external systems and/or via the internal circuitry 86) may include real-time processing suitable for guiding the operator 18 during welding activities. For example, if the operator 18 is moving the electrode 14 too slowly or too quickly, the MR eyeglasses 70 may derive or may receive derivations from external systems, to display, via the image generation system 84 certain animations, icons, warnings, text, and so on, notifying the operator 18 of the issue and/or corrective actions to take (e.g., slow down, speed up). Likewise, the speakers 44 may be used to provide audio indications suitable for improving welding operations, such as alarms, alerts, voice guidance, and the like.

Sensors 39 shown in FIGS. 4 and 5 may be communicatively coupled to the MR eyeglasses 70, directly or indirectly via another system (e.g., sensor data transmitted via power supply 12) for example, through wireless protocols (e.g., Bluetooth, IEEE 802.11x [e.g., WiFi], Zigbee, HART, LTE, Z-Wave, WirelessHD, WiGig). As mentioned above, the sensors 39 may include sensors 39 disposed on the power supply 12 (e.g., current and voltage sensors), on or about the workpiece 28 (e.g., temperature sensors, optical sensors, x-ray sensors), on the welding helmet shell 72, and on the MR eyeglasses 70 themselves (for example to monitor the operator 18). When disposed on the MR eyeglasses 70 and/or on (e.g., worn by) the operator 18, the sensors 39 may include biometric sensors suitable for detecting, for example, heat stress, heart rate (e.g., via pulse oximetry and the like), and other biometric readings of the operator 18. Accordingly, the operator 18 may be monitored, and data relayed to the operator 18 (and third parties) relating to heat stress, heart rate, and the like.

Figure 6:
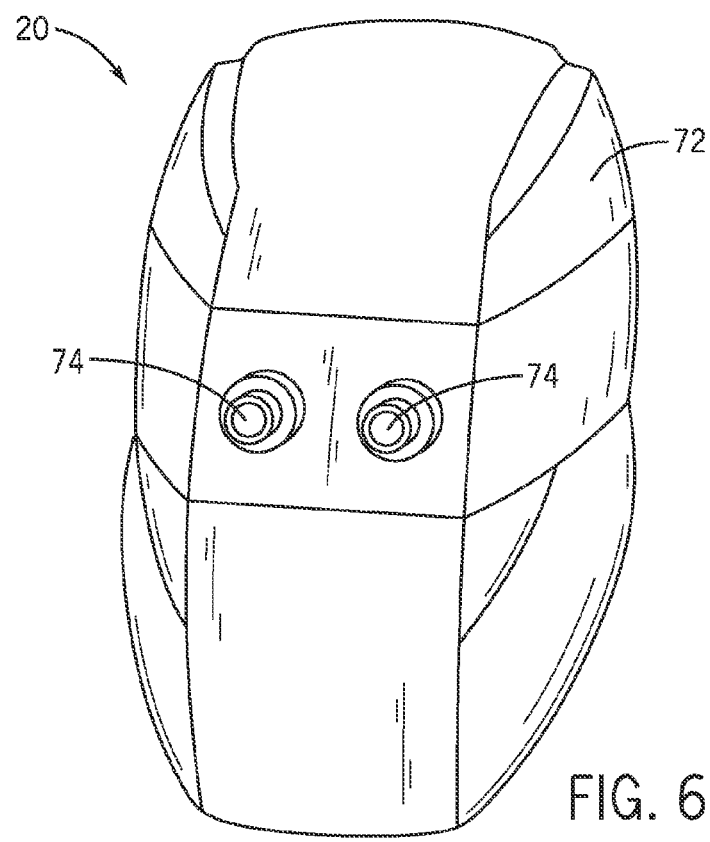
FIG. 6 is a front view of an embodiment of a protective shell included in the welding helmet system of FIG. 4, in accordance with aspects of the present disclosure.

As shown in FIG. 6 in a front view embodiment, the cameras 74 may be used in lieu of a filter screen, such as the filter screen 40. The cameras 74 may communicate with the MR eyeglasses 70, for example, via wired conduits (e.g., High-Definition Multimedia Interface [HDMI], S-video, video graphics array [VGA], and so on), via wireless protocols, such as Wireless Display (WiDi), Wireless Home Digital Interface (WHDI), Bluetooth, IEEE 802.11x (e.g., WiFi), and so on). In certain embodiments, the cameras 74 may be affixed to the shell 72 via external threads disposed on a camera housing and corresponding internal threads disposed on the shell 72, or via other mechanical fastening techniques. In another embodiment, the cameras 74 may be magnetically attached to the shell 72. Regardless of the fastening technique used, the cameras 74 may be replaceable. Accordingly, the operator 18 may select cameras 74 for specific operations. For example, higher magnification cameras (e.g., 2-20× magnification) may be selected to view smaller welds. Likewise, cameras having other optical characteristics, such as infrared or near infrared cameras may be used, which may additionally provide temperature data. In certain embodiments, the camera 74 types may be mixed. That is, one camera 74 may be a standard optical camera while a second camera 74 may be an infrared camera.

It is also to be noted that the AR eyeglasses 30 and the MR eyeglasses 70 may automatically switch into various operation modes (e.g., change functionality) based on, for example, where the eyeglasses 30 and 70 are disposed. In one example, if the eyeglasses 30, 70 are disposed inside of the shells 38, 72, then certain user biometric derivations may be computed, while eyeglasses 30, 70, not disposed in the shells 38, 72, may not derive the user biometrics unless specifically enabled by the user. Likewise, the AR eyeglasses 30 and/or the MR eyeglasses 70 may enable or disable certain functions based on the type of shells 38, 72 that they may be disposed inside of. For example, the shell 38 enables light to flow through screen 40, and thus, the AR eyeglasses 30 and/or MR eyeglasses 70 may enable modes that superimpose data over certain images (e.g., images incoming through screen 40), while when disposed on the shell 72, the AR eyeglasses 30 and/or MR eyeglasses 70 may enable modes that display data over a larger portion or all of the lenses 42 and/or displays 82. Accordingly, the AR eyeglasses 30 and the MR eyeglasses 70 may automatically adapt to their surroundings.

Figure 7:
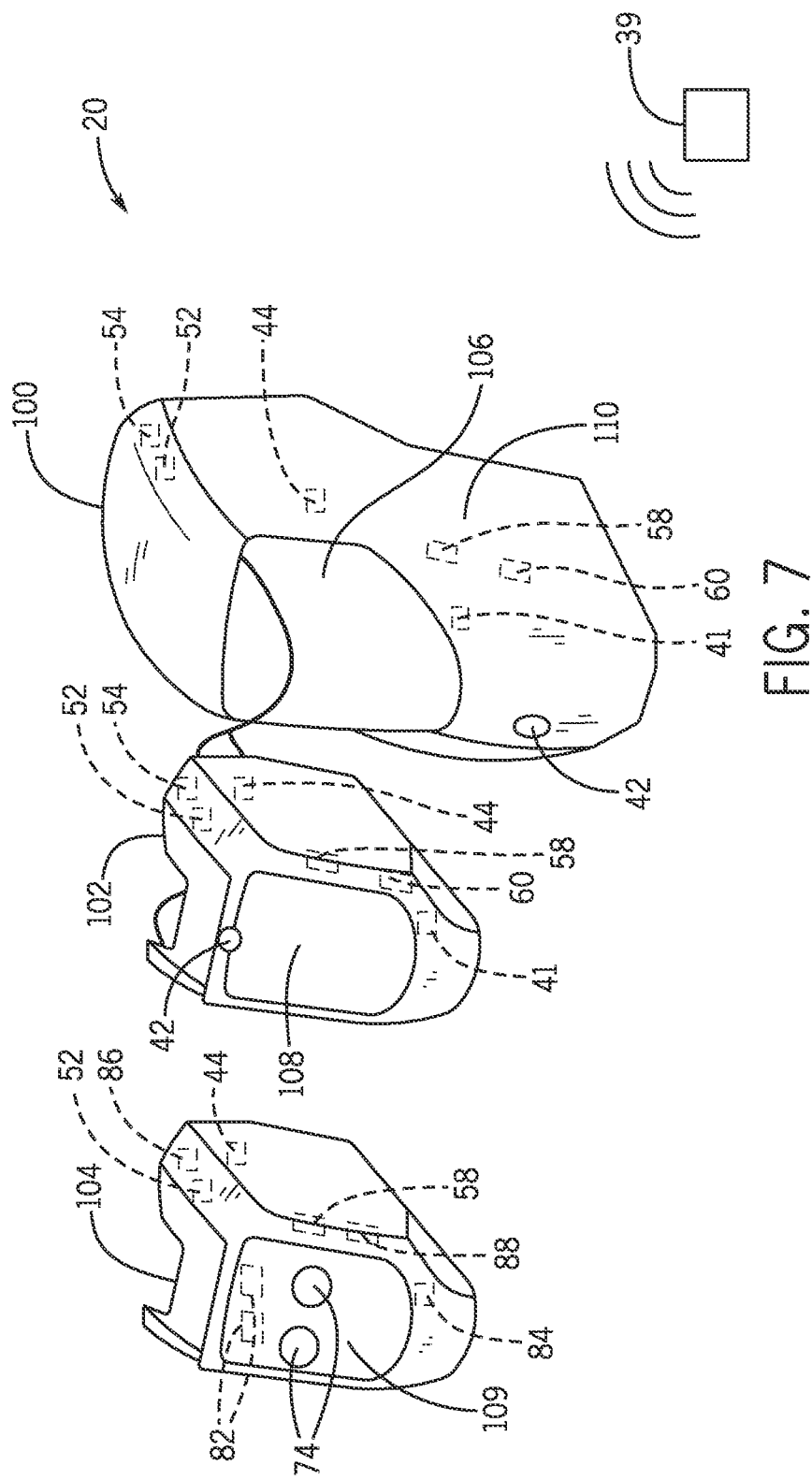
FIG. 7 is a perspective view of an embodiment of a welding helmet system having detachable augmented reality and mediated reality inserts, in accordance with aspects of the present disclosure.

FIG. 7 is a perspective view showing an embodiment of the helmet system 20 including an AR welding helmet 100, a detachable AR welding shield 102 (e.g. welding display system), and a detachable MR welding shield 104. In use, the welding shield 102 or 104 may be coupled to the helmet 100, for example, to cover an integrated grind shield 106 and to provide for AR and/or MR features similar to those provided by the AR and MR eyeglasses 30, 70. For example, in one AR embodiment, the detachable welding shield 102 may include the image generation system 41 suitable for displaying images viewable by the operator 18 and/or a trainer, as an overlay over real world images incoming through a filter screen 108. More specifically, the image generation system 41 may include projector systems, prisms, and so on, useful in delivering images viewable by the human eye through the filter screen 108.

In certain embodiments the image generation system 41 may additionally or alternatively be disposed in a shell 110. Accordingly, the grind shield 106 may display the same or similar data as the AR eyeglasses 30 and/or detachable AR welding shield 102. It is to be noted that all of the AR/MR systems 30, 70, 100, 102, 104 described herein may be user-configurable. For example, the operator 18 may set up the AR/MR systems 30, 70, 100, 102, 104 to show only certain types of data (e.g., welding metrics, user biometrics, environmental metrics) and/or alerts and alarms. Accordingly, the AR helmet system 100 may be set up by the user to only show data useful during grinding activities, while the AR/MR systems 30, 70, 102, 104 may be set up to show welding-related data.

The detachable AR welding shield 102 may include one or more cameras 42 and the detachable MR welding shield 104 may include one or more cameras 74. Likewise, the AR helmet 100 may include one or more cameras 42 disposed at various locations on the shell 108 and/or the grind shield 106. The cameras 42, 74, may be of the same type and may operate in similar fashion as when mounted on the AR eyeglasses 30 and the MR eyeglasses 70, respectively. That is, the cameras 42, 74 may capture images and/or video of welding operations and/or training activities. The cameras 42, 74 (HD camera, SD camera, thermal camera, eddy current camera) The captured images and/or video may then be used, for example, as logging data suitable for certifying a weld quality, and for further analysis. The cameras 74 (and 42), may be removable and repositionable on a shield surface 109 (e.g., via screw housings, magnetic housings, and the like), and may be communicatively coupled with the processing circuitry 86 and image generation system 84 via wired or wireless conduits (e.g., High-Definition Multimedia Interface [HDMI], S-video, video graphics array [VGA], and so on), via wireless protocols, such as Wireless Display (WiDi), Wireless Home Digital Interface (WHDI), Bluetooth, IEEE 802.11x (e.g., WiFi), and so on).

As mentioned earlier, the cameras 42 may capture imaging data for transmission to external systems (e.g., via communications system 52) for data capture and further analysis, similar to (or the same as) the data capture and analysis described above with respect to the AR eyeglasses 30. Likewise, the cameras 74 may be used for presentation of imaging data via the display(s) 82 and/or may capture imaging data for transmission to external systems (e.g., to other users), similar to the data capture and analysis described above with respect to the MR eyeglasses 70. Indeed, similar to the eyeglasses 30, 70, data from the cameras 42, 74 may be processed by the processing circuitry 54 and 86, respectively, or by external systems (e.g., power supply 12, cloud-based systems, local area network [LAN] workstations/servers, wide area network [WAN] workstation/servers) to determine, for example, a weld speed, an angle at which the operator 18 holds the electrode 14, as well as various weld observations, which, depending on a type of weld (e.g., fillet weld, groove weld, lap weld, plug and slot weld) may include concavity/convexity metrics, cross sectional weld area, leg size, toe angle, undercut metrics, weld face metrics, weld throat metrics, mismatch metrics, bead width metrics, reinforcement height metrics, porosity metrics, and so on, which may be displayed in real-time.

The camera data processing (e.g., via external systems and/or via internal systems 54, 86) may include real-time processing suitable for guiding the operator 18 during welding activities. For example, if the operator 18 is moving the electrode 14 too slowly or too quickly, the systems 100, 102, 104 may derive or may receive derivations from external systems to display, via circuitry 41 certain animations, icons, warnings, text, and so on, notifying the operator 18 of the issue and/or corrective actions to take (e.g., slow down, speed up). Likewise, the speakers 44 may be used to provide audio indications suitable for improving welding operations, such as alarms, alerts, voice guidance, and the like.

The sensors 39 may be communicatively coupled to the systems 100, 102, 104, directly or indirectly via another system (e.g., sensor data transmitted via power supply 12) for example, through wireless protocols (e.g., Bluetooth, IEEE 802.11x [e.g., WiFi], Zigbee, HART, LTE, Z-Wave, WirelessHD, WiGig). As mentioned above, the sensors 39 may include sensors 39 disposed on the power supply 12 (e.g., current and voltage sensors), on or about the workpiece 28 (e.g., temperature sensors, optical sensors, x-ray sensors), on the systems 100, 102, 104, themselves (for example to monitor the operator 18). When disposed on the systems 100, 102, 104, and/or on (e.g., worn by) the operator 18, the sensors 39 may include biometric sensors suitable for detecting, for example, heat stress, heart rate (e.g., via pulse oximetry and the like), and other biometric readings of the operator 18. Accordingly, the operator 18 may be monitored, and data relayed to the operator 18 (and third parties) relating to heat stress, heart rate, and the like.

Figure 8:
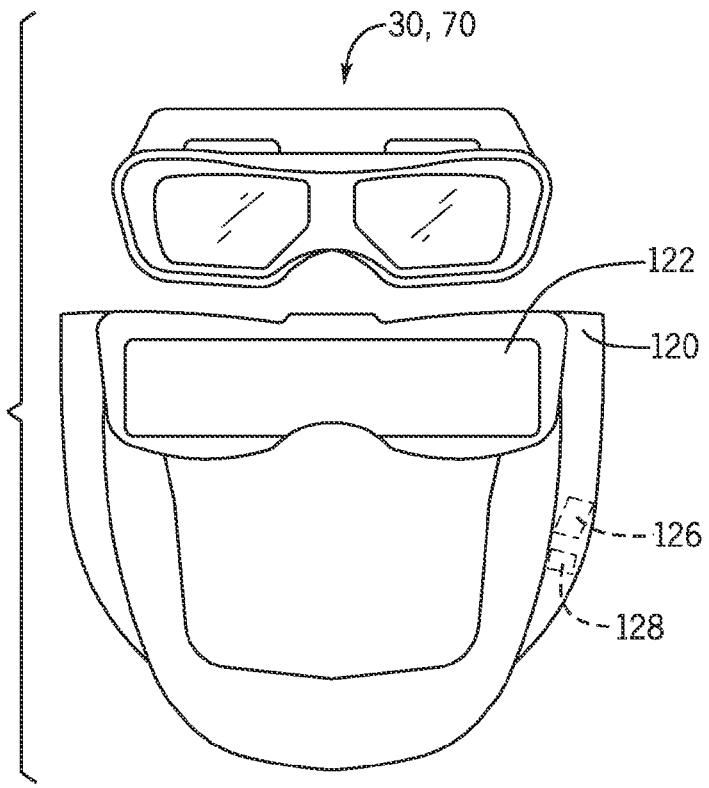
FIG. 8 is a front view of an embodiment of a face shield and AR/MR safety glasses.

Embodiments of the AR safety eyeglasses 30 and/or the MR safety eyeglasses 70 (e.g., welding display systems 30, 70) may securely coupled to a variety of protective equipment, including a protective face shield 120 (e.g., protective shell 120), shown in one embodiment in FIG. 8. Indeed, when the protective face shield 120 is selected, the user may then select the AR safety eyeglasses 30, the MR safety eyeglasses 70, or other safety glasses, and position the selected eyeglasses over the opening 122 to add enhanced protection. Various fastening techniques may be used to fasten the AR safety eyeglasses 30 and the MR safety eyeglasses 70 to the protective face shield 120. For example, an interference or friction fit between portions of the AR safety eyeglasses 30 (or portions of the MR safety eyeglasses 70) and the protective face shield 120 may securely couple the eyeglasses 30, 70 to the protective face shield 120. Additionally or alternatively, latches, Velcro™, clips, and so on, may be used to secure the AR safety eyeglasses 30 and the MR safety eyeglasses 70 to the protective face shield 120.

It is to be noted that the protective face shield 120 may, in certain embodiments, include extra batteries 124 useful for providing additional power to the AR safety eyeglasses 30 and the MR safety eyeglasses 70. Indeed, the protective face shield 120 may be operatively coupled to the AR safety eyeglasses 30 and the MR safety eyeglasses 70 to provide either extra electrical power via batteries 124 and/or extra processing power via one or more processors 126. Accordingly, detachable electrical connectors, such as magnetic connectors, pin-based connectors, and so on, may be used to electrically couple the protective face shield 120 to the AR safety eyeglasses 30 and the MR safety eyeglasses 70.

Figure 9:
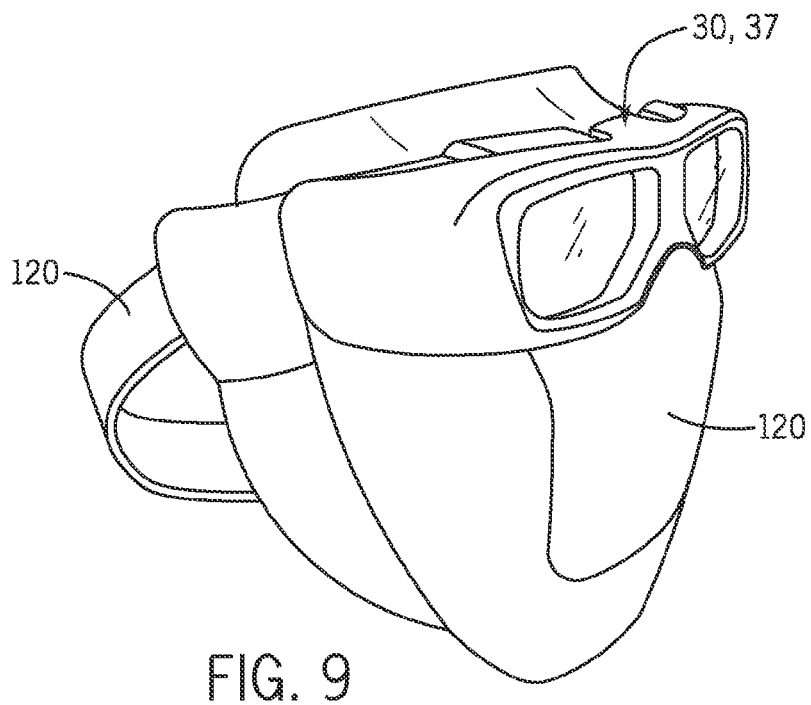
FIG. 9 is a perspective view of an embodiment of a face shield and AR/MR safety glasses of FIG. 8.

Once the AR safety eyeglasses 30 or the MR safety eyeglasses 70 are affixed onto the protective face shield 120, the entire assembly may be donned by a user, such as the operator 18, for enhanced protection. As shown in a perspective view embodiment of FIG. 9, the AR safety eyeglasses 30 and the MR safety eyeglasses 70 may include a strap 120, such as an elastic strap, suitable for securely holding the assembled eyeglasses 30, 70 and the protective face shield 120 to the operator 18. The operator 18 may then work on a desired task, and may more easily switch between the eyeglasses 30, 70, or other protective eyeglasses, when wearing the protective face shield 120. In this way, the operator 18 may select eyeglasses, such as the eyeglasses 30, 70, more suitable for a particular task, thus enhancing work efficiency, training, and safety.

While only certain features of the present disclosure have been illustrated and described herein, many modifications and changes will occur to those skilled in the art. It is, therefore, to be understood that the appended claims are intended to cover all such modifications and changes as fall within the true spirit of the present disclosure.

The invention claimed is:

1. A welding helmet system, comprising:
a protective shell; and
a welding display system configured to be removably coupled to the protective shell, wherein the welding display system is configured to be positioned on an exterior portion of the protective shell, wherein the welding display system comprises augmented reality eyeglasses, mediated reality eyeglasses, a detachable augmented reality welding shield, a detachable mediated reality welding shield, or a combination thereof, and wherein the welding display system is configured to:
receive data from a sensor; and
display a welding metric derived from the sensor.

2. The welding helmet system of claim 1, wherein the sensor comprises a camera sensor disposed on the welding display system, on the protective shell, or a combination thereof.

3. The welding helmet system of claim 1, wherein the welding display system is configured to process the data via an external system to derive the welding metric and wherein the welding display system comprises a communications system configured to communicate with a second welding display system, the external system, or a combination thereof.

4. The welding helmet system of claim 1, wherein the welding display system comprises a processor configured to process the data to derive the welding metric, a user biometric, an environmental metric, a work order data, an alarm, an alert, or a combination thereof.

5. The welding helmet system of claim 1, wherein the welding metric comprises a welding speed, a welding voltage, a welding current, a weld concavity/convexity metric, a cross sectional weld area, a weld leg size, a weld toe angle, a weld undercut metric, a weld face metric, a weld throat metric, a weld mismatch metric, a weld bead width metric, a weld reinforcement height metric, a weld porosity metric, an image, a video, or a combination thereof.

6. The welding helmet system of claim 1, wherein the welding display system is configured to:
receive second data representative of a workpiece, a welding supply, a welding system, or a combination thereof;
derive a virtual welding environment based on the second data;
display the virtual welding environment; and
enable a welding helmet wearer to manipulate the virtual welding environment.

7. A welding display system, comprising:
an image generation system;
an attachment system configured to attach and to detach the welding display system to a welding helmet, to a protective face shield, or a combination thereof; and
a processor configured to:
receive data from a sensor;
display a welding metric via the image generation system, wherein the welding metric is derived from the data; and
change the welding display system from a first operating mode to a second operating mode based on the coupling, the decoupling, or a combination thereof, of the welding display system to the welding helmet, to the protective face shield, or the combination thereof.

8. The welding display system of claim 7, wherein the welding display system comprises augmented reality eyeglasses, mediated reality eyeglasses, or a combination thereof.

9. The welding display system of claim 7, wherein the welding display system comprises a wireless communications system configured to communicate with a second welding display system, an external system, or a combination thereof.

10. The welding display system of claim 9, wherein the welding display system is configured to at least partially process the data via the external system to derive the welding metric.

11. The welding display system of claim 7, wherein the first and second operating modes each comprise a virtual reality mode, an augmented reality mode, a mediated reality mode, or a reality-only mode.

12. The welding display system of claim 7, wherein the sensor comprises a camera sensor disposed on the welding display system.

13. The welding display system of claim 7, wherein the processor is configured to process the data to derive a user biometric, an environmental metric, a work order data, an alarm, an alert, or a combination thereof.

14. The welding display system of claim 7, wherein the welding metric comprises a welding speed, a welding voltage, a welding current, a weld concavity/convexity metric, a cross sectional weld area, a weld leg size, a weld toe angle, a weld undercut metric, a weld face metric, a weld throat metric, a weld mismatch metric, a weld bead width metric, a weld reinforcement height metric, a weld porosity metric, an image, a video, or a combination thereof.

15. The welding display system of claim 7, wherein the processor is configured to:
receive second data representative of a workpiece, a welding supply, a welding system, or a combination thereof;
derive a virtual welding environment based on the second data;
display the virtual welding environment via the welding display system; and
enable a user to manipulate the virtual welding environment.

* * * * *